United States Patent
Fedorov et al.

[11] Patent Number: 5,147,284
[45] Date of Patent: Sep. 15, 1992

[54] DEVICE AND METHOD FOR RESTORATION OF VISUAL FUNCTIONS

[76] Inventors: Svyatoslav N. Fedorov, pereu lok Dostoevskogo, 1/21, kv. 32; Leonid F. Linnik, Degunimskaya ulitsa, 17, kv.36; Gennady M. Antropov, ulitsa Bolshaya Akademicheskaya, 24-a, kv.117; Nina A. Shigina, ulitsa Leskova, 30, kv.5; Vladimir I. Nikitenko, Novocherkassky bulvar, 26, kv.109; Leonid N. Arnautov, ulitsa Kharkovskaya, 11, korpus 2, kv.318; Alexandr P. Stromakov, ulitsa Matveevskaya, 1, kv.49; Irina A. Boldysheva, Abramtsevskaya ulitsa, 9, korpus 1, kv.54, all of Moscow; Valery P. Oreshkin, ulitsa 60 let VLKSM, 7, kv.98, Voronezh; Lev A. Chernyakov, ulitsa Klimashkina, 12, kv. 209, Moscow, all of U.S.S.R.

[21] Appl. No.: 565,449

[22] Filed: Aug. 9, 1990

[30] Foreign Application Priority Data

Aug. 17, 1989 [SU] U.S.S.R. .................. 4729978

[51] Int. Cl.$^5$ .............................. A61N 2/00
[52] U.S. Cl. ........................... 600/9; 600/14; 128/793; 128/421
[58] Field of Search ........................ 600/9-14; 128/783-785, 804, 793, 421

[56] References Cited

U.S. PATENT DOCUMENTS 4,603,697 8/1986 Kamerling ................ 128/421

FOREIGN PATENT DOCUMENTS 1044283 9/1983 U.S.S.R. .
1204211 1/1986 U.S.S.R. .

Primary Examiner—Lee S. Cohen
Assistant Examiner—John P. Lacyk
Attorney, Agent, or Firm—Burgess, Ryan & Wayne

[57] ABSTRACT

A device for restoration of visual functions in cases of affected optic nerve and retina comprises an electromagnetic field radiator emitting the latter field into the region of the eyeball and an electromagnetic field receiver adapted to interact with the radiator, both of them exerting an electrostimulation effect on the optic nerve and the retina. The electromagnetic field radiator is essentially a source of a pulsed magnetic field and is shaped as an electromagnet provided with an adjuster of a distance between the end of the electromagnet and the electromagnetic field receiver, which is in effect an inductor having lead wires furnished with electrodes whose active surface exceeds 10 mm$^2$. A method for restoration of visual functions in cases of affected optic nerve and retina consists in conducting electrostimulation of the eyeball, for which purpose an inductor is implanted into the orbit on the sclera of the posterior portion of the eyeball in such a manner that one of the inductor electrodes is positioned nearby the external tunic of the optic nerve, while the other electrode is fixed on the sclera in the area of the eyeball equator, whereupon a pulsed magnetic flux is applied remotely to the eyeball portion carrying the inductor, the magnetic field induction being from 0.1 T to 0.25 T, while the pulsed magnetic field is simultaneously brought in synchronism with pulsation of the internal carotid artery.

12 Claims, 3 Drawing Sheets

DEVICE AND METHOD FOR RESTORATION OF VISUAL FUNCTIONS

FIELD OF THE INVENTION

The invention relates generally to medical appliances and more specifically to devices and methods for restoration of visual functions.

The invention is applicable in ophtalmology.

BACKGROUND OF THE INVENTION

Known in the art is a system for prevention or treatment of open-angle glaucoma and presbyopia. The system comprises an active electrode implanted into the region of the ciliary muscle and electrically connected to an r.f. radiation receiver or a self-contained generator, both of which are capable of shaping electric stimuli. The electromagnetic field receiver or the self-contained generator is enclosed in a case, which is to be implanted subcutaneously in the temporal region, or into the solera, said case serving as a passive electrode, while a source of r.f. radiation serves as an electromagnetic field radiator, said source being situated outside the receiver and spaced somewhat apart therefrom. For the purpose of electrostimulation the aforesaid source shapes aperiodic pulses having a duration of 20 ms, a pulse repetition period of 1 to 3 s, and an interelectrode current of 1 $\mu$A and over (U.S. Pat. No. 4,603,691).

However, the device discussed above fails to combine electric stimuli, magnetic field and r.f. radiation for stimulation and is not adapted for improvement of visual functions in cases of affected optic nerve and retina.

One state-of-the-art method for treatment of atrophy of the optic nerve by its direct electrostimulation is known to comprise a neurosurgical procedure aimed at treatment of the intracranial portion of the optic nerve, removal of the pathologic focus, and implantation of electrodes into the optic nerve, electrostimulation being carried out through said electrodes (SU, A, 044283). However, application of the method involves a complicated and injury-inflicting neurosurgical procedure, indications for the method are much restricted, and repeated treatment courses are impracticable.

One more prior-art method for treatment of retinal dystrophy by exposing the eyeball to the effect of a static magnetic field consists in that a permanent magnet having an area of 5 to 7 cm$^2$ and magnetic induction of 0.15 to 0.2 T is applied, with its south pole, to the temporal region so that the magnet axis be aligned with a horizontal straight line passing through the external angle of the orbital margin, the treatment session lasting 15 to 20 minutes (SU, A, 1204211).

However, the method in question involves consecutive treatment of each eye separately, since simultaneous treatment of both eyes impairs their rheoophthalmic characteristics. Besides, the effect of a static magnetic field on the retina is of low efficacy, while the duration of treatment is too long.

Known in the present state of the art is also a method for sight restoration in cases of affected optic nerve, said method consisting in that electrostimulation is carried out through two electrodes, one of which is introduced into the optic nerve at the point of its emergence from the eyeball, while the other electrode is applied perilimbically and electrostimulation is effected by a number of trains of pulses, each having a duration of 250 to 1000 $\mu$s, a frequency of 25 to 100 Hz, and an intensity of 1 to 800 $\mu$A, the duration of a pulse burst being 10 to 60 s and the number of pulse bursts per train being 5 to 7, the delivery of pulses being effected in packets of five pulses in each at spacing of one second (U.S. Pat. No. 4603691).

However, introduction of an electrode into the optic nerve is a technically sophisticated and injury-inflicting procedure. Moreover, the method under consideration makes impossible repeated treatment, since the electrodes are to be removed and their reimplantation is impracticable.

In addition, a disadvantage common to all the methods discussed above resides in that only magnetic or electric stimulation is made use of for treatment.

SUMMARY OF THE INVENTION

It is a primary and essential object of the invention to provide a device and a method for restoration of visual functions, which would enable one to combine a therapeutic effect of an electric field with that of a magnetic field.

Said object is accomplished due to the fact that in a device for restoration of visual functions in cases of affected optic nerve and retina, comprising an electromagnetic field radiator emitting said field into the region of the eyeball and an electromagnetic field receiver interacting with the radiator, both said radiator and said receiver producing an effect of electrostimulation of the optic nerve and the retina, according to the invention, the electromagnetic field radiator is in effect a source of a pulsed magnetic field in the form of an electric magnet and has an adjuster of the distance between the end of the electric magnet and the electromagnetic field receiver, which is in fact an inductor whose lead wires are furnished with electrodes having an active area in excess of 10 mm$^2$.

The electric magnet may have a central magnetic field concentrator in the form of a ferrite core.

It is expedient that the distance adjuster would comprise a housing accommodating the electric magnet of the pulsed magnetic field source and a cylinder-shaped sleeve movable along the housing, and that the inductor and its lead wires be enclosed in an outer hermetically sealed insulating sheath.

It is also expedient that a ferrite core made of a high magnetic permeability material be inserted into the inductor hollow space.

Said object is accomplished also due to the fact that in a method for restoration of visual functions in cases of affected optic nerve and retina, consisting in electrostimulation of the eyeball, according to the invention, an inductor is implanted into the orbit on the sclera of the posterior eyeball portion and one of the inductor electrodes in placed close to the external tunic of the optic nerve, while the other electrode is fixed on the sclera in the area of the eyeball equator, whereupon a pulsed magnetic flux is applied remotely to the eyeball portion carrying the inductor, said flux having a magnetic field induction from 01 to 0.25 T, and the pulsed magnetic field is brought in synchronism with pulsation of the internal carotid artery.

It is expedient to select a pulsed magnetic field featuring a pulse duration from 50 a 500 ms and the rate of change of the pulsed magnetic field at the pulse leading and trailing edges within 1.0 and 50.0 ms, to carry out each treatment session as five 3 to 5-min cycles with an intercycle interval exceeding five minutes, and to conduct such sessions daily for 10 to 15 days, reiterating the treatment course after a period of time exceeding two weeks.

BRIEF DESCRIPTION OF THE DRAWINGS

In what follows the invention is illustrated by a detailed description of some specific embodiments thereof with reference to the accompanying drawings, wherein.

DETAILED DESCRIPTION OF THE INVENTION

Figure 1:
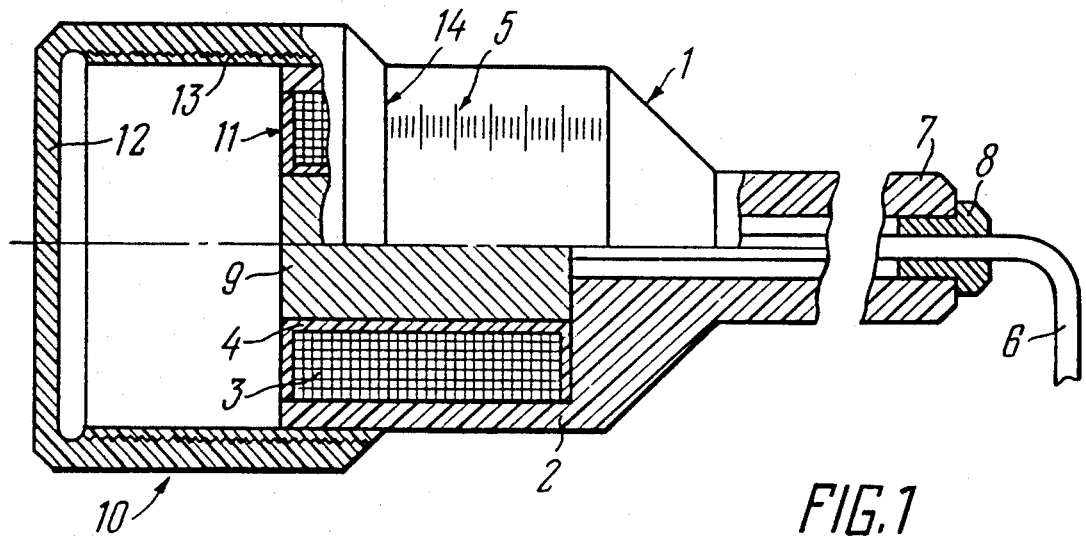
FIG. 1 a fragmentary sectional view of a radiator of the device for restoration of visual functions, according to the invention.

The device for restoration of visual functions in cases of affected optic nerve and retina comprises a magnetic field radiator that emits said field into the region of the eyeball, and an electromagnetic field receiver. The aforesaid radiator is in fact a source 1 (FIG. 1) of a pulsed magnetic field shaped as an electromagnet enclosed in a housing 2 and comprising a winding 3 arranged on a base 4. The housing 2 of the source 1 has a distance scale 5.

A power supply cable 6 runs to the electromagnet through an end 7 closed by a blank cover 8 made of an insulant. The housing 2 of the source 1 is also made of an insulant, while its winding 3, of an insulated copper wire.

The electromagnet has a magnetic field concentrator shaped as a ferrite core 9 situated in the hollow space of the base 4.

The radiator is also provided with an adjuster 10 of the distance between an electromagnet end 11 and an electromagnetic field receiver (omitted in FIG. 1). The adjuster 10 is enclosed in a housing which is essentially the housing 2 of the source 1, and a cylinder-shaped sleeve 12 movable with respect to the housing 2 with the aid of a thread 13, while an end 14 of the sleeve 12 is adapted to interact the distance scale 5 situated on the housing 2.

The electromagnetic field receiver is essentially an inductor 15 (FIGS. 2 to 6) having lead wires 16 equipped with metallic electrodes 17. The inductor 15 is enclosed in a hermetically sealed insulating sheath 18 made of, e.g., silicone, polymethylmethacrylate, or polyamide.

The electrodes 17 have an active surface over 10 mm$^2$, which is selected so as to suit a permissible current density. When the active surface of the electrodes 17 is below 10 mm$^2$ the current density would be too high and thus be causative of burns of the ocular tissue.

The inductor 15 has a diameter of 8 mm and a thickness of 0.8 mm, while the electrodes 17 are 3 mm and 8 mm long.

Figure 2:
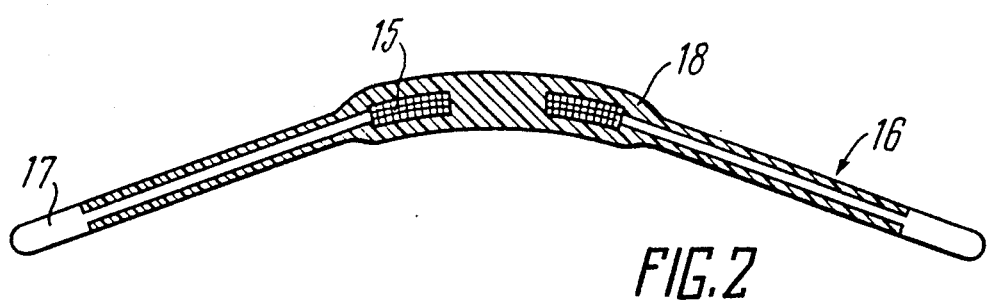
FIG. 2 is a side longitudinal sectional view of an electromagnetic field receiver of the device of FIG. 1, according to the invention.
Figure 3:
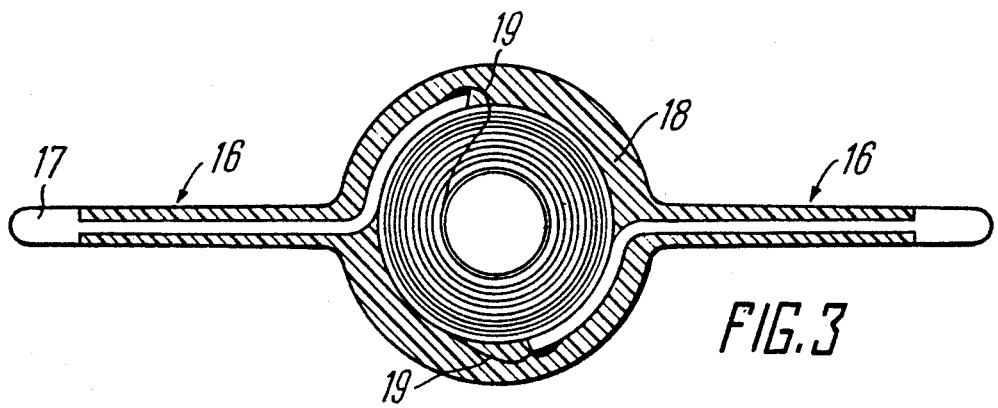
FIG. 3 is a plan sectional view of the receiver of FIG. 2.
Figure 4:
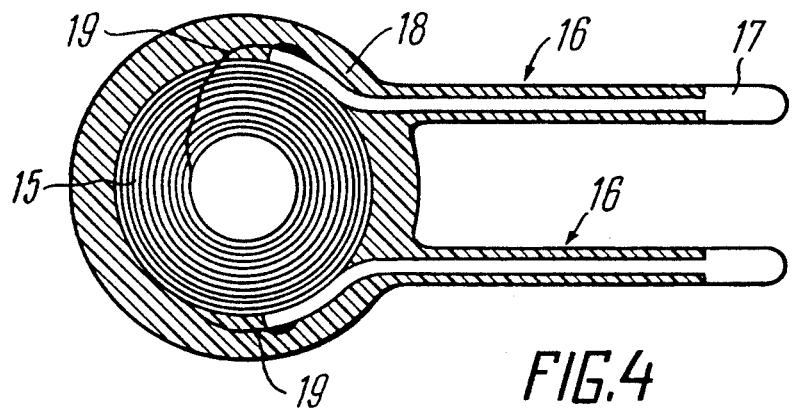
FIG. 4 is a plan sectional view of an alternative embodiment of the electromagnetic field receiver, according to the invention.
Figure 5:
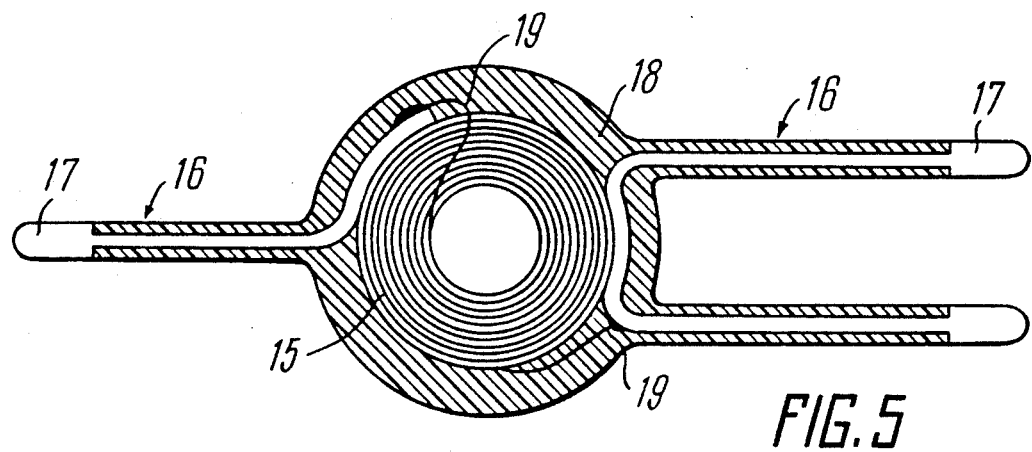
FIG. 5 is a plan sectional view of another embodiment of the electromagnetic field receiver, according to the invention.
Figure 6:
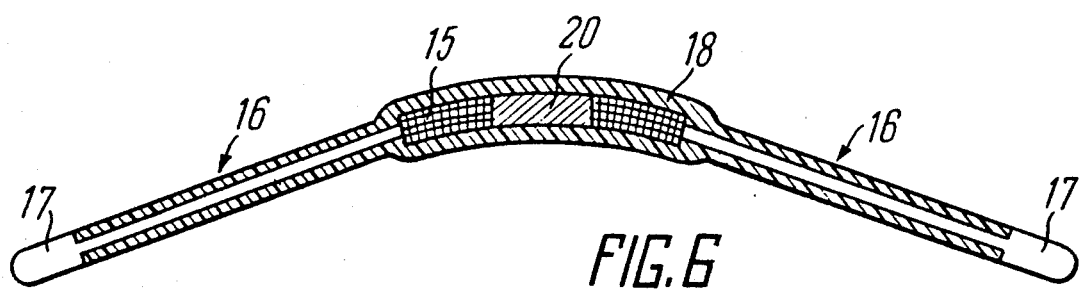
FIG. 6 a side longitudinal sectional view of the receiver together with a magnetic field concentrator, according to the invention.

The lead wires 16 of the inductor 15 are arranged symmetrically on both sides of the inductor 15 as shown in FIGS. 2 and 3. The electrodes 17 are connected to the winding of the inductor 15 through outlet wires 19. Alternatively, the lead wires 16 may be situated on one side of the inductor 15 as shown in FIG. 4. Furthermore, when use is made of the inductor 15 having three lead wires 16 their layout is presented in FIG. 5.

A ferrite core 20 (FIG. 6) is inserted into the hollow space of the inductor 15, said core being made of a high magnetic permeability material, e.g., a Ni-Co alloy or alloys based on rare-earth metals.

The inductor 15 is placed on a sclera 21 of an eyeball 22 so that the electrode $17^I$ is located nearby the external tunic of an optic nerve 23, while the other electrode $17^{II}$ is secured on the sclera 21 in the area of an equator 24 of the eyeball 22.

Figure 8:
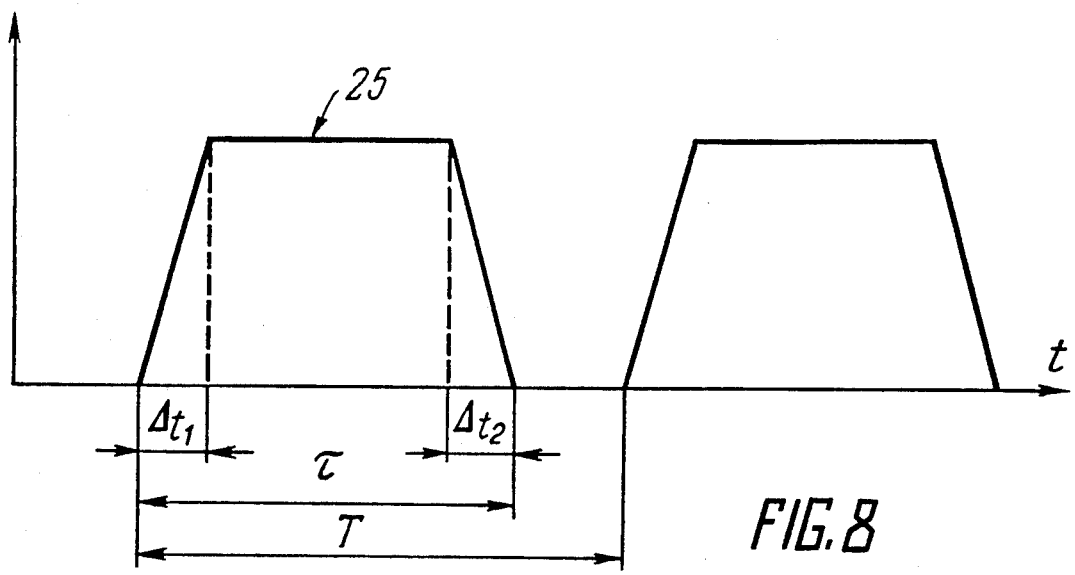
FIG. 8 is a diagram of a time-dependent variation of magnetic field intensity.

The source 1 (FIG. 1) of a pulsed magnetic field shapes pulses 25 whose time diagram is presented in FIG. 8 and which feature the duration of their leading and trailing edges equal to $\Delta t_1$ and $\Delta t_2$, respectively, a total duration $\tau$, and a pulse repetition period T, the latter being so selected as to provide synchronism of the pulsed magnetic field with pulsation of the patient's internal carotid altery. Proceeding from the aforesaid condition the repetition period T is selected to be equal to a time interval between two consecutive pulsations of the internal carotid artery.

Figure 7:
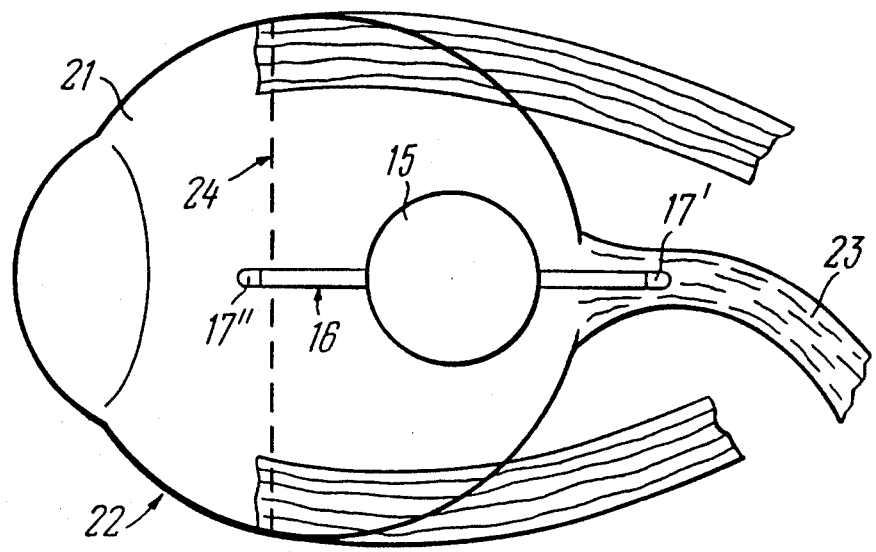
FIG. 7 shows an arrangement diagram of the electromagnetic field receiver with respect to the eyeball, according to the invention.

The magnetic field pulses 25 shaped by the source 1 (FIG. 1), are received by the inductor 15 (FIG. 2) and transmitted, via the electrodes 17 ($17^I$, $17^{II}$), to the patient's eyeball 22 (FIG. 7) to produce an electrostimulating effect on the optic nerve 23 and on the retina of the eyeball 22.

The method for restoration of visual functions in cases of affected optic nerve and retina is carried into effect as follows.

Once topic anesthesia has been carried out using Novocain or lidocaine the lids are fixed with the aid of a blepharostat and an incision is made into the conjuctiva in the inferoexternal orbit portion. The inferior and external muscles are slitched with provisional sutures. Then the posterior portion of the eyeball 22 and a part of the optic nerve are exposed, whereupon the inductor 15 is introduced into the orbit and implanted onto the sclera 21 of the posterior portion of the eyeball 22. One of the electrodes ($17^I$) of the inductor 15 is positioned close to the external tunic of the optic nerve 23 at the eyeball 22, while the other electrode ($17^{II}$) is secured on the sclera 21 in the area of the equator 24 of the eyeball 22. Next a dry antibiotic, such as penicillin, is filled in the wound and either a knotless or a noose suture is applied to the conjunctiva. Then the value of magnetic induction on the surface of the magnetic field source 1 is selected within 0.1 and 0.25 T using the adjuster 10 (FIG. 1), the magnetic field pulses 25 (FIG. 8) are brought in synchronism with pulsation of the internal carotid artery, duration of the magnetic field pulses 25 is selected within 1 and 50 ms, whereupon the electormagnetic field source 1 (FIG. 1) is placed on the outer orbit wall, and a remote effect is produced remotely on the area of location of the inductor 15 (FIG. 7) by electormagnetic pulses. Each treatment session consists of five cycles each lasting 3 to 5 minutes with an intercycle interval of at least five minutes, the sessions being carried out daily for 10 to 15 days. Whenever necessary the treatment course may be repeated in at least a two-week period.

It is worth noting that individual selection of the mode of action of a magnetic field and electric current induced in the inductor is dictated by the onset of such side effects as dizziness, headache and sensation of a high intraocular pressure, the mode of atimulation being so selected that the aforesaid side effects would not have time to appear.

Two curative factors are engaged in the proposed method, i.e., a pulsed magnetic field and an induced electric field in the form of emf arising in the inductor 15 upon passing a magnetic field pulse therethrough.

The magnetic field strength is selected on the basis of the following considerations. It is common knowledge that a magnetic field increases the lumen of minor blood vessels, reduces blood coagulability and adds to tissue oxygenation, all these effects depending on the value of the magnetic field strength. Magnetic field induction below 0.1 T on the surface of the electromagnet fails to give an adequate and persistent curative effect, since such a low induction value fails to establish an emf on the implanted inductor high enough for electric stimulation of the optic nerve and the retina. Reduced duration of the magnetic field pulse leading and trailing edges might increase the emf on the inductor, but in this case the pulse duration will decrease and therefore no stimulation will be taken by the optic nerve. Both of the effective factors with the aforesaid magnetic induction value fail to provide a new level of metabolism in the nerve, the retina and the surrounding tissues contributing to improvements of visual functions.

Magnetic field induction in excess of 0.25 T makes it necessary to cut down a total stimulation time due to an increased amount of side effects.

Reduced stimulation period due to sluggishness of changes in the metabolic processes in the optic nerve, the retina and the surrounding tissues does not allow one to breed hope for establishing a new level of dynamic equilibrium of metaboloism corresponding to a positive effect produced by magnetic field.

As a result, the velue of magnetic induction of the inductor emf proves to be too high so that necessity arises for a longer duration of the magnetic pulse edges. Accordingly, the duration of current pulses in the inductor circuit increases, too, so that the pulses become of low efficiency, since the exposure time of the optic nerve and the retina becomes too long.

The duration of a magnetic pulse within 50 and 500 ms is selected on the base of studies into hydrodynamics of minor blood vessels. Investigation of hydrodynamics of arterioles, capillaries and venules and its comparison with an electrocardiogram made it possible to detemine the optimum mean time of the systolic dilatation of minor blood vessels. Magnetic field is instrumental in prolonging the dilatation time of minor blood vessels, which results in reduced myocardial ischemia, higher velocity of erythrocytes, and in some other secondary effects. With the pulse duration below 50 ms no persistent dilatation of minor blood vessels occurs, whereas magnetic pulse duration in excess of 500 ms fails to further prolong the dilatation time of minor blood vessels.

Duration of the edges of a magnetic field pulse governs that of the emf pulses and enables one to reverse the polarity of electric pulses. Thus, for instance, in the case of a short-duration leading edge of a magnetic field pulse, a transient high-value positive emf pulse arises on the active electrode close to the external tunic of the optic nerve, whereas the trailing edge of a magnetic field pulse establishes a transient high-value negative emf pulse. In this case one of said pulses serves as a stimulation pulse for the optic nerve, while the other pulse serves as an inhibitory pulse for said nerve, with the resultant cut-down refraction time of the optic nerve axons.

In the case of a long-duration trailing edge of a magnetic field pulse a negative emf on the active electrode is of very low value and duration, with the result that a positive pulse alone will be effective. However, in the case of atrophy of the optic nerve concerned with demyelination of the optic nerve axons, formation of unipolar pulses results in a higher concentration of lipids, collagen, and some other components close to the optic nerve, whereby conditions will be provided to affect adversely the demyelination effect.

The total stimulation session time is subdivided into 3 to 5-minute cycles, which is associated with the effect of the optic nerve fatigue. It is found experimentally that in the beginning of a cycle the phenomenon of phosphene arises as the response to each of the stimuli; subsequently said phenomenon disappears, or its threshold in terms of the emf value rises. Within a five-minute interval the sensitivity of the optic nerve increases (that is, the threshold decreases), and the phenomenon of phosphene reappears. Every particular patient exhibits his/her own individual optic nerve fatigue time.

It is established that an improvement in visual functions sets in as a rule upon 7 or 8 stimulation sessions, though no persistent increase in visual functions occurs at that stage of treatment. That is why the treatment course should include at leat ten sessions. It is however worth noting that when the number of sessions exceeds 15 some untoward side effect are liable to arise, such as headache, dizziness, drowsiness, which affects adversely the curative effect of electrostimulation.

The essence of the method and of the device carrrying it into effect are now illustrated by the exemplary case histories that follow.

EXAMPLE 1

A female patient was given the diagnosis of partial atrophy of the optic nerve in the left eye.

Status on admission: prior to treatment-visual acuity OD 0.4 sph+1.5 D=0.9, OS 0.02 (primary cataract); visual field, OD-norm, OS-concentric contraction down to 20° or 30°; visual field for colours indeterminable. Computer-sided preimetry revealed reduced central photosensitivity and the presence of relative scotomas on the temporal side of the left-eye visual field, which are the symptoms of partial atrophy of the optic nerve and of macular retinopathy. An electro-ophthalmologic examination found a drastic increase in electrosensitivity thresholds and an abrupt decrease in electrolability of the left eye, which pointed to inhibition of the retinal function and of the function of the optic nerve axial bundle. Fundus oculi-OD-sound, OS-exhibited the ophthalmoscopically revealed clearcut optic disk coloured white with a greyish hue; the macular zone presented retinal degeneration.

The patient was operated upon for implantation of an inductor onto the sclera of the posterior portion of the left eyeball so that one of the electrodes was placed close to the external tunic of the optic nerve at the eyeball, while the other electrode was fixed on the sclera in the area of the eyeball equator. Then, using the respective controls on the control panel of the device, there were set the magnetic field strength of 0.1 T in the inductor, the duration of the magnetic field pulses of 50 ms, the rate of a time-dependent change in the magnetic field at the leading and trailing edges of a pulse equal to 1.0 ms, a positive pulse polarity, and a pulse repetition period equal to the pulsation rate of the internal carotid artery. An electromagnet was positioned at a preselected distance from the external wall of the left orbit, whereupon a remote effect was produced remotely on the area of location of the inductor by virtue of a pulsed magnetic field, the treatment session consisting of five 3-minute cycles with an intercycle interval of five minutes. The treatment sessions were conducted daily for 10 days.

Visual acuity in the left eye increased to 0.2 (primary cataract) after the first cycle of treatment. In a two-week period the treatment cycle was repeated, the effective parameters remaining the same. Visual acuity increased up to 0.2 sph+2.0 D=0.3, visual field for the red colour became determinable, computer-aided perimetry noticed a reduced number of relative scotomas.

Subsequently visual functions romained unaffected.

EXAMPLE 2

A male patient was given the diagnosis of partial atrophy of the left eye optic nerve secondary to circulatory disturbance in the optic disk. Conservative treatment gave but insignificant effect. Status before treatment: visual acuity, OD-0.5 (primary cataract), OS-0.1 (primary cataract). Visual field: OD-norm, OS-concentrically contacted down to 40° or 50°. Computer-aided perimetry revealed gross disturbances of the retinal photosensitivity in the macular zone. No foci of pathologic fluorescence in the macular zone were detected upon fluorescence angiography of the left eye. An electroretinographic examination of the left eye noted a higher ERG, which was an indirect symptom a pathologic condition of the optic nerve. The ocular fundus of the right eye exhibited angiosclerosis, while the ocular fundus of the left eye showed the ophthalmoscopically revealed pallid clearcut optic disk, angiosclerosis, and some deposited lipids on the temporal side of the optic disk.

The patient was operated upon for implantation of an inductor onto the sclera of posterior portion of the left eyeball so that one of the electrodes was arranged nearby the external tunic of the optic nerve, whole the other electrode was fixed on the sclera in the area of the eyeball equator. Then there were set the magnetic field strength of 0.2 T in the inductor, the duration of the magnetic field pulses of 300 ms, the rate of a time-dependent change in the magnetic field of 25 ms, an alternating pulse polarity, and a pulse repetition period equal to the pulsation rate of the internal carotid altery. Further on an electromagnet was disposed at a preselected distance from the external wall of the left orbit, whereupon a remote effect was exerted remotely on the area of location of the inductor using a pulsed magnetic field. Each of the stimulation sessions consisted of five 4-minute cycles with an intercycle interval of six minutes. The treatment sessions were carried out daily within a 12-day period. Upon completion of the stimulation session visual acuity in the left eye increased up to 0.09 sph −2.0 D=0.2.

A month later the treatment course was reiterated, the effective parameters remaining the same. Upon a repeated course of treatment visual acuity in the left eye increased up to 0.3 to 0.4 (primary cataract), while the field of vision was dilated up to 50°-60°. Subsequently visual functions remained unaffected.

EXAMPLE 3

A female patient was given the diagnosis of partial atrophy of the optic nerve in both eyes. The patient had been ill for ten years; repeated treatment courses were but of no avail.

Status before treatment: visual acuity, OD-0.4 (primary cataract); OS-0.04 (primary cataract). Visual field in both eyes contracted down to 10° on the nasal side. An electrophysiological examination established higher photosensitivity thresholds and lower electrolability, which pointed to functional inhibition of the internal retinal layers and of the optic nerve axial bundle in both eyes. Computerized tomography revealed atrophy of the optic nerve in both eyes. The oxular fundus in both eyes exhibited the ophtalmoscopically revealed pallid clearcut optic disk, the macular zone showed reticular degeneration, as well as pronounced angiosclerosis.

The patient was operated upon for implantation of an inductor onto the sclera of the left eye, followed by implantation of another inductor onto the sclera of the right eye in such a manner that one of the electrodes was situated nearby the external tunic of the optic nerve, while the other electrode was fixed on the sclera in the area of the eyeball equator. Then there were set a magnetic field strength of 0.25 T effective in the inductor, a duration of 500 ms of magnetic field pulses, a negative pulse polarity, and a pulse repetition period equal to the pulsation rate of the internal carotid artery. Further on an electromagnet was placed at a preselected distance from the external wall of the orbit, whereupon a remote effect was exerted remotely on the area of location of the inductor using a pulsed magnetic field. Then the optic nerve and the retina in both eyes were exposed to electromagnetic stimulation alternatively. Each of the stimulation sessions consisted of five 5-minute cycles with an intercycle interval of seven minutes. The sessions were carried out daily for 15 days. Upon completion of the treatment course visual acuity in the right eye increased up to 0.5 (primary cataract), that in the left eye increased up to 0.1 (primary cateract).

A month and a half later the treatment course was repeated, the action parameters remaining unaffected. Visual acuity in both eyes was the same as before, but visual field for the red and green colours became determinable.

Another month later a third treatment course was carried out, the action parameters remaining unaffected. Upon completion of the treatment course visual acuity in the right eye increased up to 0.5 or 0.6 (primary cataract), while visual activity in the left eye increased up to 0.15 (primary cataract). Visual field in both eyes dilated up to 30° on the nasal side and the findings of electrophysiological examinations became normalized.

Subsequently visual functions remained unaffected.

The proposed method and device make it possible to combine, for treatment purposes, a magnetic field and electric current induced by the inductor, the device provides for synchronism of stimuli with pulsation of the internal carotid artery; furthermore, reiterated treatment courses are also possible.

What is claimed is:

1. A device for restoration of visual functions affecting the optic nerve and retina, which comprises:
    an electromagnetic field radiator emitting said field into the region of the eyeball, said radiator including a source of a pulsed magnetic field provided with an electromagnet and a distance adjuster; and
    an electromagnetic field receiver, including an inductor; said receiver adapted to interact with said source of a pulsed magnetic field and producing an electrostimulation effect on the optic nerve and the retina; said inductor comprising a winding, lead wires and electrodes, said electrodes being connected to said lead wires and having an active surface area in excess of 10 mm$^2$;
    said distance adjuster setting a distance between said electromagnet and said receiver.

2. A device as claimed in claim 1, wherein said electromagnet comprises a central magnetic field concentrator shaped as a ferrite core.

3. A device as claimed in claim 1 or 2, wherein said distance adjuster comprises a housing including said electromagnet, and a cylinder-shaped sleeve movable lengthwise in said housing.

4. A device as claimed in claim 1 or 2, wherein said inductor and said lead wires are enclosed in an outer hermetically sealed insulating sheath.

5. A device as claimed in claim 3, wherein said inductor and said lead wires are enclosed in an outer hermetically sealed insulating sheath.

6. A device as claimed in claim 4, wherein said inductor includes a ferrite core made of a high magnetic permeability material.

7. A device as claimed in claim 5, wherein said inductor includes a ferrite core made of a high magnetic permeability material.

8. A method for the restoration of visual functions in an affected optic nerve and retina by eyeball electrostimulation, comprising: implanting an inductor having electrodes into the orbit on the sclera of the posterior portion of the eyeball with one of the inductor electrodes placed nearby the external tunic of the optic nerve, while another electrode is fixed on the sclera in the area of the equator of the eyeball; applying a pulsed magnetic flux remotely to the eyeball portion carrying the inductor, said magnetic flux comprising a magnetic field induction of from 0.1 T to 0.25 T, said pulsed magnetic field is applied in synchronism with pulsation of the internal carotid artery.

9. A method as claimed in claim 8, wherein the duration of said pulsed magnetic field is from 50 to 500 ms.

10. A method as claimed in claim 8 or 9, wherein the rate of change of said pulsed magnetic field at the leading and trailing pulse edges is from 1.0 to 50.0 ms.

11. A method as claimed in claim 8 or 9, wherein each treatment session comprises five 3 to 5 minute cycles with an intercycle interval greater than five minutes, said sessions are carried out daily for 10 to 15 days, the treatment course being reiterated after a period of time exceeding two weeks.

12. A method as claimed in claim 10, wherein each treatment session incorporates five 3 to 5 minute cycles with an intercycle interval greater than five minutes, said sessions are carried out daily for 10 to 15 days, the treatment course being reiterated after a period of time exceeding two weeks.

* * * * *